US007949543B2

(12) United States Patent
Chan et al.

(10) Patent No.: US 7,949,543 B2
(45) Date of Patent: May 24, 2011

(54) METHODS, SYSTEMS, AND COMPUTER PROGRAM PRODUCTS FOR PROMOTING HEALTHCARE INFORMATION TECHNOLOGIES TO CARD MEMBERS

(75) Inventors: Cheung Tat Chan, Fanwood, NJ (US); Andrew L. Gorrin, New York, NY (US); Nancy E. Hood, Brooklyn, NY (US)

(73) Assignee: Oltine Acquisitions NY LLC, Dover, DE (US)

( * ) Notice: Subject to any disclaimer, the term of this patent is extended or adjusted under 35 U.S.C. 154(b) by 702 days.

(21) Appl. No.: 11/674,437

(22) Filed: Feb. 13, 2007

(65) Prior Publication Data

US 2008/0195415 A1    Aug. 14, 2008

(51) Int. Cl.
*G06Q 10/00* (2006.01)
*G06Q 50/00* (2006.01)

(52) U.S. Cl. ................ 705/2; 705/4; 705/3; 705/14.3

(58) Field of Classification Search .................. 705/2–4, 705/14.3
See application file for complete search history.

(56) References Cited

U.S. PATENT DOCUMENTS

| | | | |
|---|---|---|---|
| 4,491,725 A | 1/1985 | Pritchard |
| 4,713,761 A | 12/1987 | Sharpe et al. |
| 4,858,121 A | 8/1989 | Barber et al. |
| 4,916,611 A | 4/1990 | Doyle et al. |
| 5,235,507 A | 8/1993 | Sackler et al. |
| 5,301,105 A | 4/1994 | Cummings, Jr. |
| 5,532,464 A | 7/1996 | Josephson et al. |
| 5,550,734 A | 8/1996 | Tarter et al. |
| 5,583,760 A | 12/1996 | Klesse |
| 5,704,044 A | 12/1997 | Tarter et al. |
| 5,740,425 A | 4/1998 | Povilus |
| 5,826,243 A | 10/1998 | Musmanno et al. |
| 5,832,447 A | 11/1998 | Rieker et al. |
| 5,857,079 A | 1/1999 | Claus et al. |
| 5,873,069 A | 2/1999 | Reuhl et al. |
| 5,878,141 A | 3/1999 | Daly et al. |
| 5,903,830 A | 5/1999 | Joao et al. |
| 5,930,759 A | 7/1999 | Moore et al. |
| 5,945,653 A | 8/1999 | Walker et al. |
| 6,012,035 A | 1/2000 | Freeman, Jr. et al. |
| 6,042,005 A | 3/2000 | Basile et al. |

(Continued)

OTHER PUBLICATIONS

Cybear ("Cybear Group Reports Third Quarter 2001 Results of Operations." Business Editors & Health/Medical/Technology Writers. Business Wire. New York: Oct. 25, 2001. p. 1).*

(Continued)

*Primary Examiner* — Linh Michelle Le
(74) *Attorney, Agent, or Firm* — Sterne, Kessler, Goldstein & Fox P.L.L.C.

(57) ABSTRACT

The disclosed methods, systems, and computer-program products allow a credit or charge card issuer to promote healthcare information technology (HIT) products to physician card members that are affiliated with a healthcare organization, such as a preferred-provider organization (PPO). In an embodiment, the PPO endorses at least one HIT product, such as an electronic medical record (EMR), and the PPO identifies the endorsed HIT product to a transactional card provider. The transactional card provider then identifies at least one supplier of the endorsed HIT product and negotiates a discount on the endorsed HIT product when purchased from identified HIT supplier using a financial transaction instrument issued by the transactional card provider. The financial transaction instrument may be provided to the physician card member, who may purchase the endorsed HIT product from the identified supplier at the negotiated discount.

25 Claims, 4 Drawing Sheets

U.S. PATENT DOCUMENTS

| | | |
|---|---|---|
| 6,108,641 A | 8/2000 | Kenna et al. |
| 6,112,986 A | 9/2000 | Berger et al. |
| 6,154,732 A | 11/2000 | Tarbox |
| 6,208,973 B1 | 3/2001 | Boyer et al. |
| 6,249,772 B1 | 6/2001 | Walker et al. |
| 6,292,786 B1 | 9/2001 | Deaton et al. |
| 6,339,766 B1 | 1/2002 | Gephart |
| 6,341,265 B1 | 1/2002 | Provost et al. |
| 6,343,271 B1 | 1/2002 | Peterson et al. |
| 6,343,279 B1 | 1/2002 | Bissonette et al. |
| 6,353,811 B1 | 3/2002 | Weissman |
| 6,386,450 B1 | 5/2002 | Ogasawara |
| 6,394,341 B1 | 5/2002 | Mäkipää et al. |
| 6,418,441 B1 | 7/2002 | Call |
| 6,422,462 B1 | 7/2002 | Cohen |
| 6,442,526 B1 | 8/2002 | Vance et al. |
| 6,442,532 B1 | 8/2002 | Kawan |
| 6,488,205 B1 | 12/2002 | Jacobson |
| 6,543,683 B2 | 4/2003 | Hoffman |
| 6,594,640 B1 | 7/2003 | Postrel |
| 6,601,761 B1 | 8/2003 | Katis |
| 6,615,190 B1 | 9/2003 | Slater |
| 6,637,649 B2 | 10/2003 | Walsh |
| 6,662,999 B1 | 12/2003 | Vancour et al. |
| 6,671,358 B1 | 12/2003 | Seidman et al. |
| 6,749,114 B2 | 6/2004 | Madani |
| 6,776,332 B2 | 8/2004 | Allen et al. |
| 6,820,058 B2 | 11/2004 | Wood et al. |
| 6,820,059 B2 | 11/2004 | Wood et al. |
| 6,879,959 B1 | 4/2005 | Chapman et al. |
| 6,898,598 B2 | 5/2005 | Himmel et al. |
| 6,932,268 B1 | 8/2005 | McCoy et al. |
| 6,947,900 B2 | 9/2005 | Giordano, III et al. |
| 6,999,943 B1 | 2/2006 | Johnson et al. |
| 7,039,593 B2 | 5/2006 | Sager |
| 7,072,842 B2 | 7/2006 | Provost et al. |
| 7,097,098 B2 | 8/2006 | Roberts |
| 7,104,443 B1 | 9/2006 | Paul et al. |
| 7,133,840 B1 | 11/2006 | Kenna et al. |
| 7,158,955 B2 | 1/2007 | Diveley et al. |
| 7,174,302 B2 | 2/2007 | Patricelli et al. |
| 7,197,468 B1 | 3/2007 | Patricelli et al. |
| 7,213,750 B1 | 5/2007 | Barnes et al. |
| 7,233,942 B2 | 6/2007 | Nye |
| 7,249,097 B2 | 7/2007 | Hutchison et al. |
| 7,249,112 B2 | 7/2007 | Berardi et al. |
| 7,263,493 B1 | 8/2007 | Provost et al. |
| 7,268,667 B2 | 9/2007 | Beenau et al. |
| 7,268,668 B2 | 9/2007 | Beenau et al. |
| 7,333,937 B2 | 2/2008 | Baldwin, Jr. et al. |
| 7,346,522 B1 | 3/2008 | Baylor et al. |
| 7,380,707 B1 | 6/2008 | Fredman |
| 7,392,224 B1 | 6/2008 | Bauer et al. |
| 7,434,729 B2 | 10/2008 | Cracchiolo et al. |
| 7,493,266 B2 | 2/2009 | Gupta |
| 7,499,875 B1 | 3/2009 | May et al. |
| 7,566,000 B2 | 7/2009 | Agostino et al. |
| 7,624,026 B2 | 11/2009 | DiPiero et al. |
| 7,650,308 B2 | 1/2010 | Nguyen et al. |
| 2001/0014873 A1 | 8/2001 | Henderson et al. |
| 2001/0034618 A1 | 10/2001 | Kessler et al. |
| 2002/0016764 A1 | 2/2002 | Hoffman |
| 2002/0019885 A1 | 2/2002 | Sleeper |
| 2002/0035529 A1 | 3/2002 | Tooke |
| 2002/0087444 A1 | 7/2002 | DiPiero et al. |
| 2002/0099659 A1 | 7/2002 | Swentor |
| 2002/0116206 A1 | 8/2002 | Chatani |
| 2002/0128879 A1 | 9/2002 | Spears |
| 2002/0147678 A1 | 10/2002 | Drunsic |
| 2002/0174030 A1 | 11/2002 | Praisner et al. |
| 2002/0198831 A1 | 12/2002 | Patricelli et al. |
| 2002/0198833 A1 | 12/2002 | Wohlstadter |
| 2003/0018567 A1 | 1/2003 | Flitcroft et al. |
| 2003/0023498 A1 | 1/2003 | Benton |
| 2003/0023549 A1 | 1/2003 | Armes et al. |
| 2003/0033272 A1 | 2/2003 | Himmel et al. |
| 2003/0061153 A1 | 3/2003 | Birdsong et al. |
| 2003/0061358 A1 | 3/2003 | Piazza et al. |
| 2003/0065561 A1 | 4/2003 | Brown et al. |
| 2003/0069760 A1 | 4/2003 | Gelber |
| 2003/0088487 A1 | 5/2003 | Cheng et al. |
| 2003/0097331 A1 | 5/2003 | Cohen |
| 2003/0119554 A1 | 6/2003 | Horn |
| 2003/0126094 A1 | 7/2003 | Fisher et al. |
| 2003/0130948 A1 | 7/2003 | Algiene et al. |
| 2003/0135459 A1 | 7/2003 | Abelman et al. |
| 2003/0187695 A1 | 10/2003 | Drennan |
| 2003/0195769 A1 | 10/2003 | Francis |
| 2003/0195773 A1 | 10/2003 | Mahaffey |
| 2003/0200118 A1 | 10/2003 | Lee et al. |
| 2003/0216997 A1 | 11/2003 | Cohen |
| 2003/0225678 A1 | 12/2003 | Understein |
| 2004/0010449 A1 | 1/2004 | Berardi et al. |
| 2004/0010462 A1 | 1/2004 | Moon et al. |
| 2004/0049425 A1 | 3/2004 | Bakker et al. |
| 2004/0083183 A1 | 4/2004 | Hardesty et al. |
| 2004/0098328 A1 | 5/2004 | Grant et al. |
| 2004/0098351 A1 | 5/2004 | Duke |
| 2004/0117302 A1 | 6/2004 | Weichert et al. |
| 2004/0138999 A1 | 7/2004 | Friedman et al. |
| 2004/0238622 A1 | 12/2004 | Freiberg |
| 2004/0243464 A1 | 12/2004 | Beck |
| 2004/0249745 A1 | 12/2004 | Baaren |
| 2005/0015280 A1 | 1/2005 | Gabel et al. |
| 2005/0027607 A1 | 2/2005 | Pearson |
| 2005/0033677 A1 | 2/2005 | Birdsong et al. |
| 2005/0038740 A1 | 2/2005 | Ogilvie |
| 2005/0043992 A1 | 2/2005 | Cohagan et al. |
| 2005/0065873 A1 | 3/2005 | Hendrickson et al. |
| 2005/0075931 A1 | 4/2005 | Pearson |
| 2005/0080692 A1 | 4/2005 | Padam et al. |
| 2005/0098621 A1 | 5/2005 | de Sylva |
| 2005/0102181 A1 | 5/2005 | Scroggie et al. |
| 2005/0144071 A1 | 6/2005 | Monahan et al. |
| 2005/0144074 A1 | 6/2005 | Fredregill et al. |
| 2005/0256794 A1 | 11/2005 | Colby |
| 2005/0261968 A1 | 11/2005 | Randall et al. |
| 2005/0288964 A1 | 12/2005 | Lutzen et al. |
| 2006/0027647 A1 | 2/2006 | Deane et al. |
| 2006/0036523 A1 | 2/2006 | Stover et al. |
| 2006/0064332 A1 | 3/2006 | Schoenbaum et al. |
| 2006/0076400 A1 | 4/2006 | Fletcher |
| 2006/0080144 A1 | 4/2006 | Goel et al. |
| 2006/0085335 A1 | 4/2006 | Crawford et al. |
| 2006/0113376 A1 | 6/2006 | Reed et al. |
| 2006/0143052 A1 | 6/2006 | Fotsch et al. |
| 2006/0149595 A1* | 7/2006 | Williams et al. .................. 705/2 |
| 2006/0149670 A1 | 7/2006 | Nguyen et al. |
| 2006/0167720 A1 | 7/2006 | Harrison et al. |
| 2006/0173777 A1 | 8/2006 | Torres et al. |
| 2006/0253324 A1* | 11/2006 | Miller ............................ 705/14 |
| 2006/0277075 A1* | 12/2006 | Salwan ............................ 705/3 |
| 2006/0287914 A1 | 12/2006 | Shelley |
| 2007/0007335 A1 | 1/2007 | Cracchiolo et al. |
| 2007/0011025 A1 | 1/2007 | Cracchiolo et al. |
| 2007/0011088 A1 | 1/2007 | Cracchiolo et al. |
| 2007/0011089 A1 | 1/2007 | DeSchryver |
| 2007/0023504 A1 | 2/2007 | Blankenship et al. |
| 2007/0033070 A1 | 2/2007 | Beck et al. |
| 2007/0106607 A1 | 5/2007 | Seib et al. |
| 2007/0119920 A1 | 5/2007 | Hogg et al. |
| 2007/0168279 A1 | 7/2007 | D'Angelo |
| 2007/0175985 A1 | 8/2007 | Barnes et al. |
| 2007/0179813 A1 | 8/2007 | Darling |
| 2007/0185799 A1 | 8/2007 | Harrison et al. |
| 2007/0185800 A1 | 8/2007 | Harrison et al. |
| 2007/0185801 A1 | 8/2007 | Harrison et al. |
| 2007/0185802 A1 | 8/2007 | Harrison et al. |
| 2007/0185803 A1 | 8/2007 | Harrison et al. |
| 2007/0194108 A1 | 8/2007 | Kalappa et al. |
| 2007/0194109 A1 | 8/2007 | Harrison et al. |
| 2007/0203757 A1 | 8/2007 | Dibiasi et al. |
| 2007/0265961 A1 | 11/2007 | Shah et al. |
| 2008/0011820 A1 | 1/2008 | Brown et al. |
| 2008/0110971 A1 | 5/2008 | Pover et al. |
| 2008/0156868 A1 | 7/2008 | Slen et al. |

2008/0179395 A1 7/2008 Dixon et al.
2008/0195423 A1 8/2008 Baylor et al.
2008/0210751 A1 9/2008 Kim

OTHER PUBLICATIONS

Fisher ("Cary, N.C., Medical Technology Firm May Get Boost from Doctors' Endorsement." Jean P. Fisher. Knight Ridder Tribune Business News. Washington: Nov. 13, 2003. p. 1).*
Alonso, G. et al., "Enhancing the Fault Tolerance of Workflow Management Systems," *IEEE Concurrency*, pp. 74-81 (Jul.-Sep. 2000).
Haase et al., U.S. Appl. No. 11/770,367, filed Jun. 28, 2007, entitled "Universal Rollover Account".
Harrison et al., U.S. Appl. No. 11/698,955, filed Jan. 29, 2007, entitled "Filtered Healthcare Payment Card Linked to Tax-Advantaged Accounts".
Jagatic et al., U.S. Appl. No. 11/561,326, filed Dec. 17, 2006, entitled "Variable Revenue Sharing for Multiple Account Payment Instruments".
Jagatic et al., U.S. Appl. No. 11/675,478, filed Feb. 15, 2007, entitled "Transmission and Capture of Line-Item-Detail to Assist in Transaction Substantiation and Matching".
Keck et al., U.S. Appl. No. 11/675,438, filed Feb. 15, 2007, entitled "Practice Management System (PMS) Integration".
Keck et al., U.S. Appl. No. 11/675,456, filed Feb. 15, 2007, entitled "Practice Management System (PMS) Integration".
Keck et al., U.S. Appl. No. 11/768,708, filed Jun. 26, 2007, entitled "Accelerated Payments for Health Care Plans".
Schoenberg, "Internet Based Repository of Medical Records That Retains Patient Confidentiality," *British Medical Journal*, vol. 321, Issue 7270, pp. 1199-1203 (Nov. 11, 2000).
Richardson, P., "Online broker woos real estate agents; Amerihall's fees lower than those of brick-and-mortar firms," Highbeam Research, Oct. 30, 2000, printed from http:www.highbeam.com/doc/1G1-66668508.html, 4 pages.
Bell, A., "Web Sites Push Medical Services Shopping. (Brief Article)," National Underwriter Property & Casualty-Risk & Benefits Management, Aug. 21, 2000, printed from http://www.highbeam.com/doc/1G1-65106694.html, 4 pages.
Gal-Or, E., The profitability of vertical mergers between hospitals and physician practices, Journal of Health Economics, vol. 18, Issue 5, pp. 623-624 (Oct. 1999).
Health Savings Custodial Account Agreement, Trust Administrators, Inc., 1970 Broadway, Suite 1140, Oakland, California, downloaded from www.trustadmin.com/public_html/graphics/CustodialAgreement.pdf, 3 pages.
Ruess, Court Snarls MTF Claims Payment Now in Limbo; [All Editions], Trenton Bureau, The Record, Bergen County, N.J.: Feb. 24, 1994, p. a.01.
Office Communication, dated Mar. 26, 2010, for U.S. Appl. No. 11/275,403, filed Dec. 29, 2005, 16 pages.
Office Communication, dated Jun. 4, 2010, for U.S. Appl. No. 11/381,641, filed May 4, 2006, 6 pages.
Office Communication, dated Mar. 17, 2010, for U.S. Appl. No. 11/461,356, filed Jul. 31, 2006, 13 pages.
Office Communication, dated Aug. 5, 2010, for U.S. Appl. No. 11/461,356, filed Jul. 31, 2006, 22 pages.
Office Communication, dated Apr. 8, 2010, for U.S. Appl. No. 11/461,365, filed Jul. 31, 2006, 9 pages.
Office Communication, dated Jun. 8, 2010, for U.S. Appl. No. 11/461,374, filed Jul. 31, 2006, 14 pages.
Office Communication, dated Jun. 7, 2010, for U.S. Appl. No. 11/461,389, filed Jul. 31, 2006, 10 pages.
Office Communication, dated Feb. 5, 2010, for U.S. Appl. No. 11/461,394, filed Jul. 31, 2006, 12 pages.
Office Communication, dated May 12, 2010, for U.S. Appl. No. 11/461,396, filed Jul. 31, 2006, 27 pages.
Office Communication, dated Mar. 31, 2010, for U.S. Appl. No. 11/561,326, filed Nov. 17, 2006, 10 pages.
Office Communication, dated Apr. 20, 2010, for U.S. Appl. No. 11/675,478, filed Feb. 15, 2007, 9 pages.
Office Communication, dated Mar. 30, 2010, for U.S. Appl. No. 11/698,955, filed Jan. 29, 2007, 12 pages.
Office Communication, dated Jan. 26, 2010, for U.S. Appl. No. 11/768,708, filed Jun. 26, 2007, 14 pages.
Office Communication, dated Dec. 24, 2009, for U.S. Appl. No. 11/770,367, filed Jun. 28, 2007, 25 pages.
Office Communication, dated Jun. 24, 2010, for U.S. Appl. No. 11/770,367, filed Jun. 28, 2007, 25 pages.
Office Communication, dated May 21, 2010, for U.S. Appl. No. 12/558,386, filed Sep. 1, 2009, 15 pages.
Breitkopf, D., "Card Issuers Jacking Up Phone Fees," *American Banker*, SourceMedia, Inc., Highbeam Research, printed Aug. 28, 2010 from <http://www.highbeam.com>, 2 pages (Publication Date: Jun. 30, 2003).
Gal-Or, E., "The profitability of vertical mergers between hospitals and physician practices," *Journal of Health Economics*, vol. 18, Issue 5, pp. 623-654 (Oct. 1999).
Office Communication, dated Sep. 28, 2010, for U.S. Appl. No. 11/275,403, filed Dec. 29, 2005, 15 pages.
Office Communication, dated Sep. 10, 2010, for U.S. Appl. No. 11/461,394, filed Jul. 31, 2006, 13 pages.
Office Communication, dated Aug. 31, 2010, for U.S. Appl. No. 11/461,396, filed Jul. 31, 2006, 16 pages.
Office Communication, dated Sep. 1, 2010, for U.S. Appl. No. 11/561,326, filed Nov. 17, 2006, 7 pages.
Office Communication, dated Oct. 12, 2010, for U.S. Appl. No. 12/558,386, filed Sep. 1, 2009, 19 pages.
Office Communication, dated Nov. 8, 2010, for U.S. Appl. No. 11/275,401, filed Dec. 29, 2005, 10 pages.
Office Communication, dated Nov. 4, 2010, for U.S. Appl. No. 11/461,374, filed Jul. 31, 2006, 17 pages.
Office Communication, dated Oct. 19, 2010, for U.S. Appl. No. 11/675,478, filed Feb. 15, 2007, 9 pages.
Harrison et al., U.S. Appl. No. 12/558,386, filed Sep. 11, 2009, entitled "Healthcare Card Incentive Program for Multiple Users".
Office Communication, dated Feb. 26, 2009, for U.S. Appl. No. 11/381,641, filed May 4, 2006, 12 pages.
Notice of Allowance, dated Aug. 6, 2009, for U.S. Appl. No. 11/381,641, filed May 4, 2006, 6 pages.
Office Communication, dated Mar. 10, 2009, for U.S. Appl. No. 11/275,399, filed Dec. 29, 2005, 6 pages.
Office Communication, dated Oct. 5, 2009, for U.S. Appl. No. 11/275,399, filed Dec. 29, 2005, 9 pages.
Office Communication, dated May 8, 2009, for U.S. Appl. No. 11/275,401, filed Dec. 29, 2005, 5 pages.
Office Communication, dated Oct. 14, 2009, for U.S. Appl. No. 11/275,401, filed Dec. 29, 2005, 8 pages.
Office Communication, dated Sep. 27, 2007, for U.S. Appl. No. 11/275,403, filed Dec. 29, 2005, 7 pages.
Office Communication, dated Mar. 12, 2008, for U.S. Appl. No. 11/275,403, filed Dec. 29, 2005, 14 pages.
Office Communication, dated Jun. 13, 2008, for U.S. Appl. No. 11/275,403, filed Dec. 29, 2005, 11 pages.
Office Communication, dated Dec. 12, 2008, for U.S. Appl. No. 11/275,403, filed Dec. 29, 2005, 11 pages.
Office Communication, dated Jun. 11, 2009, for U.S. Appl. No. 11/275,403, filed Dec. 29, 2005, 12 pages.
Office Communication, dated Oct. 6, 2006, for U.S. Appl. No. 11/275,405, filed Dec. 29, 2005, 5 pages.
Office Communication, dated May 1, 2007, for U.S. Appl. No. 11/275,405, filed Dec. 29, 2005, 11 pages.
Office Communication, dated Nov. 13, 2007, for U.S. Appl. No. 11/275,405, filed Dec. 29, 2005, 11 pages.
Notice of Allowance, dated Jun. 12, 2008, for U.S. Appl. No. 11/275,405, filed Dec. 29, 2005, 7 pages.
Office Communication, dated Jun. 15, 2006, for U.S. Appl. No. 10/904,639, filed Nov. 19, 2004, 8 pages.
Notice of Allowance, dated Dec. 28, 2006, for U.S. Appl. No. 10/904,639, filed Nov. 19, 2004, 6 pages.
Office Communication, dated Sep. 2, 2008, for U.S. Appl. No. 11/461,365, filed Jul. 31, 2006, 7 pages.
Office Communication, dated Feb. 23, 2009, for U.S. Appl. No. 11/461,365, filed Jul. 31, 2006, 8 pages.
Office Communication, dated Jul. 14, 2009, for U.S. Appl. No. 11/461,365, filed Jul. 31, 2006, 7 pages.

Office Communication, dated Sep. 29, 2008, for U.S. Appl. No. 11/461,374, filed Jul. 31, 2006, 7 pages.
Office Communication, dated Feb. 26, 2009, for U.S. Appl. No. 11/461,374, filed Jul. 31, 2006, 8 pages.
Office Communication, dated Jul. 15, 2009, for U.S. Appl. No. 11/461,374, filed Jul. 31, 2006, 11 pages.
Office Communication, dated Apr. 27, 2009, for U.S. Appl. No. 11/461,389, filed Jul. 31, 2006, 5 pages.
Notice of Allowance, dated Sep. 18, 2009, for U.S. Appl. No. 11/461,389, filed Jul. 31, 2006, 6 pages.
Office Communication, dated Jun. 20, 2008, for U.S. Appl. No. 11/461,392, filed Jul. 31, 2006, 17 pages.
Notice of Allowance, dated May 14, 2009, for U.S. Appl. No. 11/461,392, filed Jul. 31, 2006, 7 pages.
Office Communication, dated Sep. 4, 2008, for U.S. Appl. No. 11/461,394, filed Jul. 31, 2006, 13 pages.
Office Communication, dated May 26, 2009, for U.S. Appl. No. 11/461,394, filed Jul. 31, 2006, 15 pages.
Office Communication, dated Aug. 3, 2009, for U.S. Appl. No. 11/461,394, filed Jul. 31, 2006, 2 pages.
Office Communication, dated Jul. 2, 2008, for U.S. Appl. No. 11/461,396, filed Jul. 31, 2006, 26 pages.
Office Communication, dated Feb. 5, 2009, for U.S. Appl. No. 11/461,396, filed Jul. 31, 2006, 10 pages.
Office Communication, dated Jul. 27, 2009, for U.S. Appl. No. 11/461,396, filed Jul. 31, 2006, 25 pages.
Office Communication, dated Oct. 27, 2009, for U.S. Appl. No. 11/461,396, filed Jul. 31, 2006, 2 pages.
Office Communication, dated Sep. 26, 2007, for U.S. Appl. No. 11/675,438, filed Feb. 15, 2007, 9 pages.
Office Communication, dated Mar. 13, 2008, for U.S. Appl. No. 11/675,438, filed Feb. 15, 2007, 14 pages.
Office Communication, dated Jul. 6, 2009, for U.S. Appl. No. 11/768,708, filed Jun. 26, 2007, 14 pages.
Office Communication, dated Jan. 23, 2008, for U.S. Appl. No. 11/675,478, filed Feb. 15, 2007, 8 pages.
Office Communication, dated Aug. 11, 2008, for U.S. Appl. No. 11/675,478, filed Feb. 15, 2007, 9 pages.
Office Communication, dated Nov. 17, 2008, for U.S. Appl. No. 11/675,478, filed Feb. 15, 2007, 3 pages.
Office Communication, dated Mar. 31, 2009, for U.S. Appl. No. 11/675,478, filed Feb. 15, 2007, 9 pages.
Office Communication, dated Oct. 27, 2009, for U.S. Appl. No. 11/675,478, filed Feb. 15, 2007, 9 pages.
Office Communication, dated Jul. 20, 2009, for U.S. Appl. No. 11/698,955, filed Jan. 29, 2007, 6 pages.
Office Communication, dated Nov. 10, 2009, for U.S. Appl. No. 11/698,955, filed Jan. 29, 2007, 17 pages.
Office Communication, dated Sep. 27, 2007, for U.S. Appl. No. 11/675,456, filed Feb. 15, 2007, 9 pages.
Office Communication, dated Mar. 13, 2008, for U.S. Appl. No. 11/675,456, filed Feb. 15, 2007, 11 pages.
Office Communication, dated Oct. 29, 2008, for U.S. Appl. No. 11/770,367, filed Jun. 28, 2007, 6 pages.
Office Communication, dated Jan. 6, 2009, for U.S. Appl. No. 11/770,367, filed Jun. 28, 2007, 21 pages.
Office Communication, dated Jun. 10, 2009, for U.S. Appl. No. 11/770,367, filed Jun. 28, 2007, 21 pages.
Office Communication, dated Oct. 7, 2009, for U.S. Appl. No. 11/770,367, filed Jun. 28, 2007, 2 pages.
Notice of Allowance, dated Nov. 30, 2009, for U.S. Appl. No. 11/381,641, filed May 4, 2006, 7 pages.
Office Communication, dated Nov. 24, 2009, for U.S. Appl. No. 11/275,403, filed Dec. 29, 2005, 7 pages.
Office Communication, dated Dec. 1, 2009, for U.S. Appl. No. 11/461,374, filed Jul. 31, 2006, 11 pages.

* cited by examiner

METHODS, SYSTEMS, AND COMPUTER PROGRAM PRODUCTS FOR PROMOTING HEALTHCARE INFORMATION TECHNOLOGIES TO CARD MEMBERS

BACKGROUND

1. Field of the Invention

This invention generally relates to healthcare information technology products, and in particular, it relates to methods for promoting electronic medical records in medical practices.

2. Related Art

Medical records are essential to every medical practice, and the vast majority of these records are maintained in paper form using a system that has remained unchanged for decades. However, with the passage of the Health Insurance Portability and Accountability Act (HIPAA), the United States government has encouraged physicians to adopt healthcare information technology (HIT) modules, such as electronic medical records (EMRs), to operate their practices by 2010. Further, there is speculation that legislation may mandate a deadline by which physicians who transact business with governmental healthcare agencies must adopt HIT modules within their practices. The impact of such legislation would be widely felt, as patients supported by governmental healthcare agencies such as Medicare form a large part of many medical practices.

Electronic medical records (EMRs) possess a number of advantages over traditional, handwritten medical records. EMRs are inherently portable, and as such, they are easily transferred from physician to physician when a patient relocates. The accessibility of EMRs also makes them attractive for use in hospital settings in which a number of physicians or practitioners may view and modify a single set of records. Further, recent technological advantages, such as tablet-based notebook computers, powerful wireless internet connections, and longer-life batteries, have made EMRs more accessible to physicians in private practice.

However, significant barriers block the wider adoption of EMRs within many medical practices, and one such barrier is the incorporation of a patient's paper medical record into a corresponding EMR. The conversion of these physical records into EMRs is an expensive and time-consuming process that must accurately capture the content of the physical record. As many of these records contain extensive handwritten content that may have been generated by different healthcare professionals over the life span of the patient, some of the content may be illegible following conversion. Further, the material may exist in any number of formats, sizes, media types and qualities, which further complicates accurate conversion.

SUMMARY OF THE INVENTION

Accordingly, the present disclosure introduces methods, systems, and computer-program products for promoting healthcare information technology products to card members.

According to various embodiments of the disclosed processes, at least one healthcare information technology product is endorsed by an organization and is identified to a physician associated with the organization. The organization may be any combination of a preferred-provider organization (PPO) and a health maintenance organization (HMO), and the at least one healthcare information technology product may comprise an electronic medical record. The physician is then provided with a financial transaction instrument for purchasing the at least one healthcare information technology product at a discounted price. The physician may also be provided an opportunity to become a card member, and upon the physician's becoming a card member, an additional discount may be provided to the physician on the at least one healthcare information technology product when purchased with the financial transaction instrument.

Further features and advantages of the present invention as well as the structure and operation of various embodiments of the present invention are described in detail below with reference to the accompanying drawings.

BRIEF DESCRIPTION OF THE DRAWINGS

The features of the present invention will become more apparent from the detailed description set forth below when taken in conjunction with the drawings. The left-most digit of a reference number identifies the drawing in which the reference number first appears.

DETAILED DESCRIPTION

Figure 1:
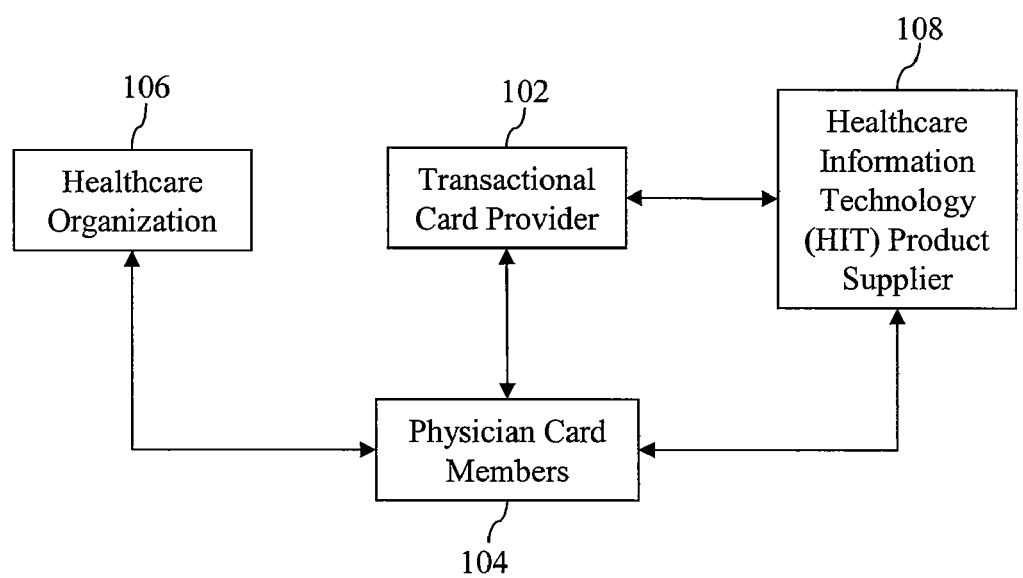
FIG. 1 is a detailed illustration of an exemplary partnership that promotes the adoption of healthcare information technology products.

The present invention, as described below, may be implemented in many different embodiments of software, hardware, firmware, and/or the entities illustrated in the figures. Any actual software code with the specialized control of hardware to implement the present invention is not limiting of the present invention. Thus, the operational behavior of the present invention will be described with the understanding that modifications and variations of the embodiments are possible, given the level of detail presented herein.

I. Terminology

The terms "user", "end user", "consumer", "customer", "participant", and/or the plural form of these terms are used interchangeably throughout herein to refer to those persons or entities capable of accessing, using, being affected by and/or benefiting from the tool described herein.

Furthermore, the terms "business" or "merchant" may be used interchangeably with each other and shall mean any person, entity, distributor system, software and/or hardware that is a provider, broker and/or any other entity in the distribution chain of goods or services. For example, a merchant may be a grocery store, a retail store, a travel agency, a service provider, an on-line merchant or the like.

A "transaction account" as used herein refers to an account associated with an open account or a closed account system (as described below). The transaction account may exist in a physical or non-physical embodiment. For example, a transaction account may be distributed in non-physical embodiments such as an account number, frequent-flyer account, telephone calling account or the like. Furthermore, a physical embodiment of a transaction account may be distributed as a financial instrument. The terms "account provider" or "financial institution" as used herein refer to the financial institution associated with the account.

A financial transaction instrument may be traditional plastic transaction cards, titanium-containing, or other metal-containing, transaction cards, clear and/or translucent transaction cards, foldable or otherwise unconventionally-sized transaction cards, radio-frequency enabled transaction cards, or other types of transaction cards, such as credit, charge, debit, pre-paid or stored-value cards, or any other like financial transaction instrument. A financial transaction instrument may also have electronic functionality provided by a network of electronic circuitry that is printed or otherwise incorporated onto or within the transaction instrument (and typically referred to as a "smart card"), or be a fob having a transponder and an RFID reader.

"Open cards" are financial transaction cards that are generally accepted at different merchants. Examples of open cards include the American Express®, Visa®, MasterCard® and Discover® cards, which may be used at many different retailers and other businesses. In contrast, "closed cards" are financial transaction cards that may be restricted to use in a particular store, a particular chain of stores or a collection of affiliated stores. One example of a closed card is a pre-paid gift card that may only be purchased at, and only be accepted at, a clothing retailer, such as The Gap® store.

Stored value cards are forms of transaction instruments associated with transaction accounts, wherein the stored value cards provide cash equivalent value that may be used within an existing payment/transaction infrastructure. Stored value cards are frequently referred to as gift, pre-paid or cash cards, in that money is deposited in the account associated with the card before use of the card is allowed. For example, if a customer deposits ten dollars of value into the account associated with the stored value card, the card may only be used for payments together totaling no more than ten dollars.

With regard to use of a transaction account, users may communicate with merchants in person (e.g., at the box office), telephonically, or electronically (e.g., from a user computer via the Internet). During the interaction, the merchant may offer goods and/or services to the user. The merchant may also offer the user the option of paying for the goods and/or services using any number of available transaction accounts. Furthermore, the transaction accounts may be used by the merchant as a form of identification of the user. The merchant may have a computing unit implemented in the form of a computer-server, although other implementations are possible.

In general, transaction accounts may be used for transactions between the user and merchant through any suitable communication means, such as, for example, a telephone network, intranet, the global, public Internet, a point of interaction device (e.g., a point of sale (POS) device, personal digital assistant (PDA), mobile telephone, kiosk, etc.), online communications, off-line communications, wireless communications, and/or the like.

Persons skilled in the relevant arts will understand the breadth of the terms used herein and that the exemplary descriptions provided are not intended to be limiting of the generally understood meanings attributed to the foregoing terms.

II. Overview

The processes now introduced allow a credit, debit, stored value, charge, or transactional card provider, such as American Express Company, Inc., of New York, N.Y., to promote the adoption of healthcare information technology (HIT) products among its physician card members. In embodiments of such processes, a healthcare organization endorses a particular HIT product, which is then identified to a transactional card provider. The transactional card provider then identifies at least one supplier of the endorsed HIT product that accepts financial transaction instruments issued by the transactional card provider. The transactional card provider then negotiates discounts on the endorsed HIT product when purchased by physician card members using the financial transaction instruments. The endorsed HIT products and the financial transaction instruments with discounts on the endorsed HIT products are directly marketed to physicians associated with the healthcare organization. Physician card members then obtain a discount on the endorsed HIT products when purchasing the products using the financial transaction instrument. Further, the transactional card provider may provide physicians associated with the healthcare organization an additional discount on the endorsed HIT product upon becoming a card member.

III. Methods, Systems, and Computer-Program Products for Promoting Healthcare Information Technologies to Card Members FIG. 1 illustrates an exemplary three-way partnership 100 through which a transactional card provider 102 encourages the adoption of healthcare information technology (HIT) products among its physician card members. Within the exemplary partnership of FIG. 1, transactional card provider 102, such as American Express, has a number of physician card members 104 that may be affiliated with a healthcare organization 106. Physician card members 104 may also form a portion of a customer base for a HIT product supplier 108, and HIT product supplier 108 may accept financial transaction instruments issued by transactional card provider 102.

Healthcare organization 106 may be composed of a plurality of physician members, and healthcare organization 106 may collectively negotiate partnerships with additional insurance companies and pharmaceutical manufacturers on behalf of its physician members. In one embodiment, healthcare organization 106 is a preferred-provider organization (PPO) that may be composed of a plurality of physician members that provide healthcare services for a reduced fee. Alternatively, healthcare organization 106 may be a health-maintenance organization (HMO) having a plurality of physician members. In other embodiments, healthcare organization 106 may be any additional governmental organization or private entity that has a plurality of affiliated physicians or healthcare providers. Although the invention will be described herein with reference to a PPO, one of skill in the art will recognize that other healthcare organizations may be used without departing from the spirit and scope of the present invention.

Figure 2:
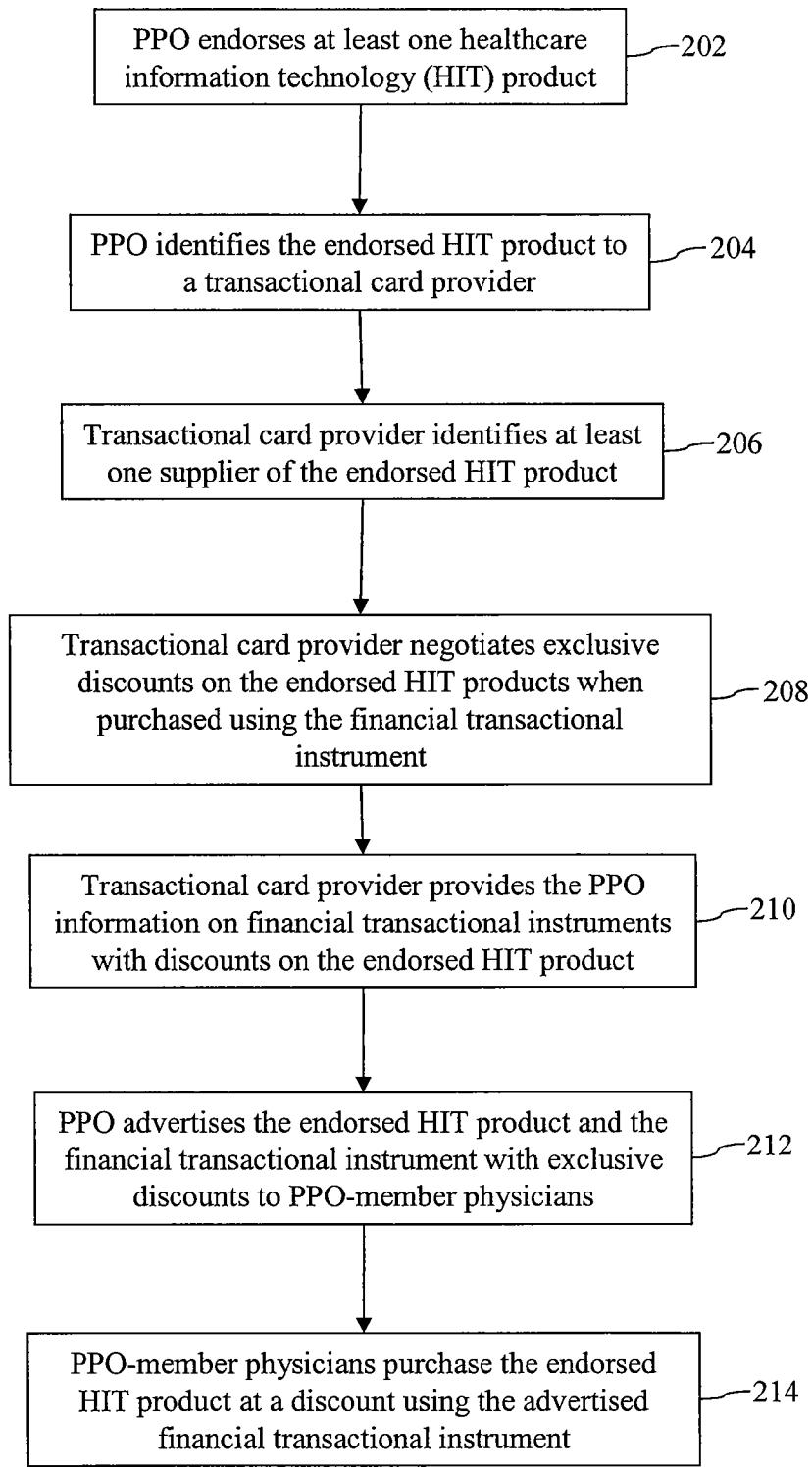
FIG. 2 is a detailed illustration of an exemplary method for promoting the adoption of healthcare information technology products.

FIG. 2 illustrates a method for promoting healthcare information technology (HIT) products that may be practiced within the exemplary partnership of FIG. 1. In step 202, a healthcare organization, such as a preferred-provider organization (PPO), endorses at least one HIT product for use by members of the PPO. The endorsed HIT product may be an electronic medical record (EMR), the use of which may bring the physician into compliance with proposed Federal regulations.

The PPO then identifies the at least one endorsed HIT product to a transactional card provider, such as transactional card provider 102, in step 204. The transactional card provider in turn identifies at least one supplier of the endorsed HIT product in step 206. The identified HIT product supplier may accept financial transaction instruments that are issued by the transactional card provider.

In step 208, the transactional card provider negotiates with the identified HIT product supplier to obtain a discount on the endorsed HIT product when that HIT product is purchased with a financial transaction instrument issued by the transactional card provider. The discount negotiated within step 208 may be exclusive to a single transaction instrument, and the discount may be linked with the financial transaction instrument to produce a single payment product that facilitates the purchase of the endorsed HIT product.

The transactional card provider, in step 210, provides the PPO information regarding the financial transaction instrument coupled with exclusive discounts on the endorsed HIT product, and the PPO may utilize this information to launch a marketing campaign directed to its member physicians in step 212. The marketing campaign may advertise the endorsed HIT product to the physician members of the PPO, and it may additionally advertise the financial transaction instrument with exclusive discounts on endorsed HIT products.

Then, in step 214, the PPO-member physicians are provided an opportunity to purchase the endorsed HIT product at a discounted price using the financial transaction instrument. Further, those PPO-member physicians who are not card members of the transactional card provider are afforded an opportunity to become card members and obtain access to the financial transaction instrument with exclusive discounts on the endorsed HIT product. If these PPO-member physicians become card members, the transactional card provider may apply an additional credit to the purchase of the endorsed HIT product using the financial transaction instrument.

Figure 3:
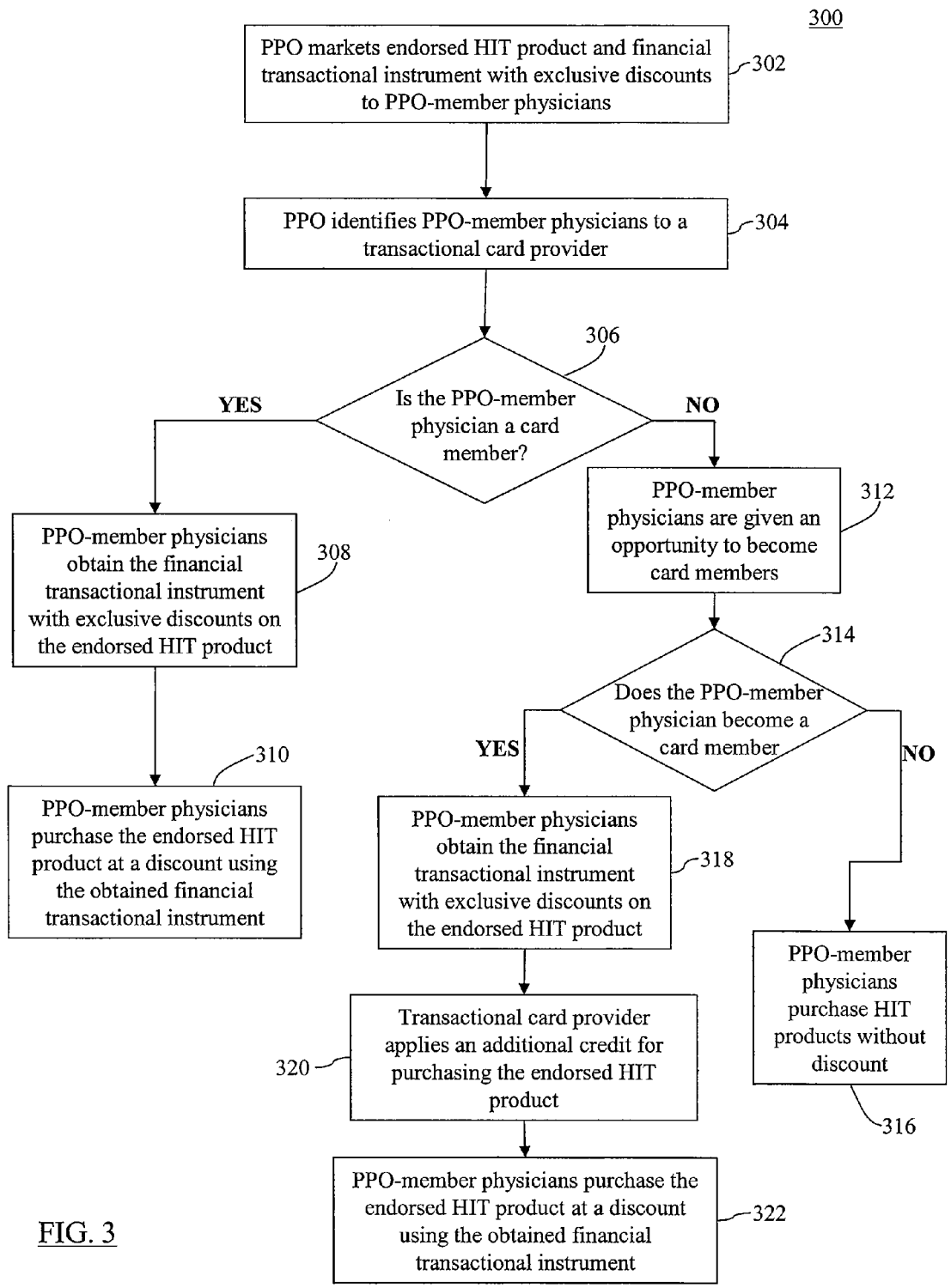
FIG. 3 is a detailed illustration of an exemplary method for purchasing healthcare information technology products that may be incorporated into the exemplary method of FIG. 2.

FIG. 3 illustrates a purchasing method that may be incorporated within the exemplary method of FIG. 2. In step 302, physician members of a healthcare organization, such as a preferred-provider organization (PPO), receive targeted marketing from the PPO regarding an endorsed healthcare information technology (HIT) product and a financial transaction instrument that may be used to purchase the endorsed product at a discounted rate. The PPO then identifies these PPO-member physicians to a transactional card provider in step 304, and the transactional card provider then determines in step 306 whether each of the PPO-member physicians is a card member and has access to the financial transaction instrument.

If the transactional card provider determines that a PPO-member physician is a card member in step 306, then the PPO-member physician may obtain the financial transaction instrument with exclusive discounts on the endorsed HIT product from the transactional card provider in step 308. The transactional card provider may also link the exclusive discounts on the endorsed HIT products to an existing financial transaction instrument held by the PPO-member physician in step 308. The PPO-member physician may then purchase the endorsed HIT product from an identified HIT product supplier at a discounted rate using the obtained financial transaction instrument in step 310.

However, if the transactional card provider determines in step 306 that the PPO-member physician is not a card member, then the PPO-member physician is given an opportunity to become a card member and obtain access to the financial transaction instrument in step 312. The transactional card provider then determines whether the PPO-member physician has become a card member in step 314.

If the PPO-member physician declines to become a card member, then the PPO-member physician does not obtain access to the financial transaction instrument with the exclusive discount on the endorsed HIT product, and the member physician may choose to purchase the endorsed HIT product or a different HIT product without the discount in step 316.

If the PPO-member physician becomes a card member, then the PPO-member physician may obtain the financial transaction instrument with exclusive discounts on the endorsed HIT product from the transactional card provider in step 318. Further, in step 320, the transactional card provider may apply an additional credit to the purchase of the endorsed HIT product using the obtained financial transaction instrument. The PPO-member physician may then purchase the endorsed HIT product in step 322 using the newly-obtained financial transaction instrument with exclusive discounts on the endorsed HIT product and the additional credit provided by the transactional card provider upon the physician's becoming a card member.

IV. Exemplary Computer Systems

Figure 4:
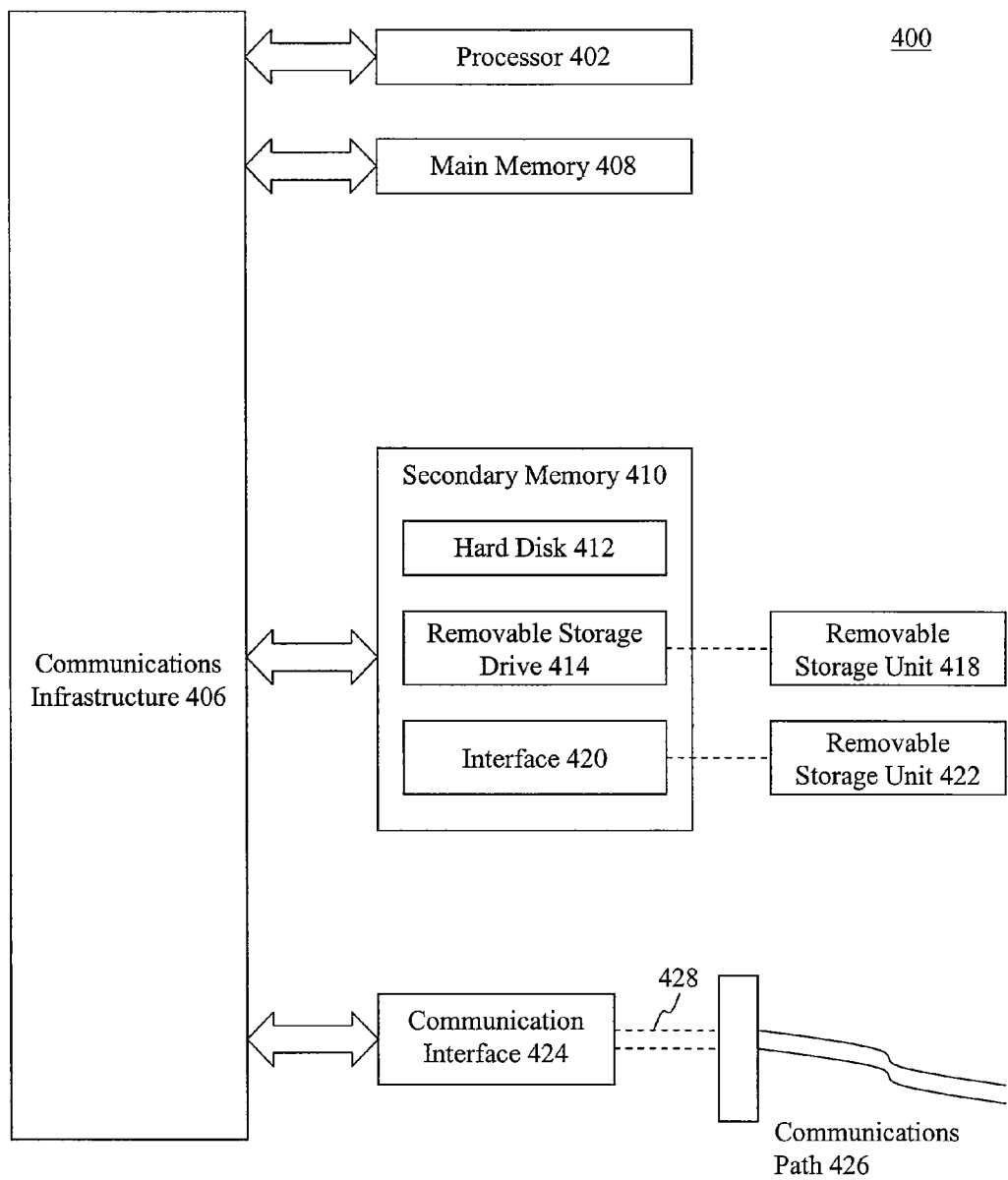
FIG. 4 is a block diagram of an exemplary computer connected to a network with which the exemplary method of FIG. 2 may be implemented.

FIG. 4 is a diagram of an exemplary computer system 400 upon which the present invention may be implemented. The exemplary computer system 400 includes one or more processors, such as processor 402. The processor 402 is connected to a communication infrastructure 406, such as a bus or network. Various software implementations are described in terms of this exemplary computer system. After reading this description, it will become apparent to a person skilled in the relevant art how to implement the invention using other computer systems and/or computer architectures.

Computer system 400 also includes a main memory 408, preferably random access memory (RAM), and may include a secondary memory 410. The secondary memory 410 may include, for example, a hard disk drive 412 and/or a removable storage drive 414, representing a magnetic tape drive, an optical disk drive, etc. The removable storage drive 414 reads from and/or writes to a removable storage unit 418 in a well-known manner. Removable storage unit 418 represents a magnetic tape, optical disk, or other storage medium that is read by and written to by removable storage drive 414. As will be appreciated, the removable storage unit 418 can include a computer usable storage medium having stored therein computer software and/or data.

In alternative implementations, secondary memory 410 may include other means for allowing computer programs or other instructions to be loaded into computer system 400. Such means may include, for example, a removable storage unit 422 and an interface 420. An example of such means may include a removable memory chip (such as an EPROM, or PROM) and associated socket, or other removable storage units 422 and interfaces 420, which allow software and data to be transferred from the removable storage unit 422 to computer system 400.

Computer system 400 may also include one or more communications interfaces, such as communications interface 424. Communications interface 424 allows software and data to be transferred between computer system 400 and external devices. Examples of communications interface 424 may include a modem, a network interface (such as an Ethernet card), a communications port, a PCMCIA slot and card, etc. Software and data transferred via communications interface 424 are in the form of signals 428, which may be electronic, electromagnetic, optical or other signals capable of being received by communications interface 424. These signals 428 are provided to communications interface 424 via a communications path (i.e., channel) 426. This channel 426 carries signals 428 and may be implemented using wire or cable, fiber optics, an RF link and other communications channels. In an embodiment of the invention, signals 428 comprise data packets sent to processor 402. Information representing processed packets can also be sent in the form of signals 428 from processor 402 through communications path 426.

The terms "computer program medium" and "computer usable medium" are used to refer generally to media such as removable storage units 418 and 422, a hard disk installed in hard disk drive 412, and signals 428, which provide software to the computer system 400.

Computer programs are stored in main memory 408 and/or secondary memory 410. Computer programs may also be received via communications interface 424. Such computer programs, when executed, enable the computer system 400 to implement the present invention as discussed herein. In particular, the computer programs, when executed, enable the processor 402 to implement the present invention. Where the invention is implemented using software, the software may be stored in a computer program product and loaded into computer system 400 using removable storage drive 414, hard drive 412 or communications interface 424.

V. CONCLUSION

The disclosed processes encourage the wider adoption of healthcare information technology (HIT) products while providing a value-added benefit for physicians, healthcare organizations, HIT product suppliers, and transactional card providers. Physician card members receive substantial discounts on government-mandated HIT products, thus allowing them to cost-effectively meet their regulatory obligations and keep a large share of their patient volume. Further, healthcare organizations provide relevant value to their membership base by utilizing both discounts on HIT products and the marketing expertise of the transactional card provider to increase organizational membership and loyalty. Through the disclosed processes, partner merchants, such as HIT product suppliers, gain a cost-effective and efficient way to increase sales to their target customers while continuing to sell additional products that increase sales and customer loyalty. The disclosed processes also allow the transactional card provider to acquire new card members and to capture incremental HIT spending using financial transaction instruments issued by the transactional card provider.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. Thus, the present invention should not be limited by any of the above described exemplary embodiments, but should be defined only in accordance with the following claims and their equivalents.

In addition, it should be understood that the figures illustrated in the attachments, which highlight the functionality and advantages of the present invention, are presented for example purposes only. The architecture of the present invention is sufficiently flexible and configurable, such that it may be utilized (and navigated) in ways other than that shown in the accompanying figures.

Further, the purpose of the following Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present invention in any way.

What is claimed is:

1. A method comprising:
    receiving, using a computing device of a transactional card provider, information regarding an endorsement of a healthcare information technology product by a healthcare organization;
    identifying, using the computing device, a supplier of the healthcare information technology product that accepts a card issued by the transactional card provider;
    negotiating, with the supplier and using the computing device, a discount that applies when the healthcare information technology product is purchased with the card; and
    sending, using the computing device, a message to the healthcare organization, wherein the message contains information regarding the discount.

2. The method of claim 1, wherein the message further comprises information regarding an additional discount that applies to a physician that purchases the healthcare information technology product using the card.

3. The method of claim 2, wherein the healthcare information technology product is designed to bring the physician into compliance with a governmental regulation.

4. The method of claim 2, further comprising:
    advertising, to the physician, at least one of:
        the card, or
        the healthcare information technology product.

5. The method of claim 1, wherein the healthcare organization comprises a preferred-provider organization (PPO) or a health maintenance organization (HMO).

6. The method of claim 1, wherein the healthcare information technology product comprises an electronic medical record.

7. The method of claim 2, wherein the message further comprises information regarding a second discount that applies once the physician becomes a new cardmember.

8. A system comprising:
    a processor; and
    a memory storing instructions, execution of which by a computing device causes the computing device to perform operations comprising:
        receiving, at a transactional card provider, information regarding an endorsement of a healthcare information technology product by a healthcare organization,
        identifying a supplier of the healthcare information technology product that accepts a card issued by the transactional card provider,
        negotiating, with the supplier, a discount that applies when the healthcare information technology product is purchased with the card, and
        sending a message to the healthcare organization, wherein the message contains information regarding the discount.

9. The system of claim 8, wherein the message further comprises information regarding an additional discount that applies to a physician that purchases the healthcare information technology product using the card.

10. The system of claim 9, wherein the healthcare information technology product is designed to bring the physician into compliance with a governmental regulation.

11. The system of claim 9, wherein the operations further comprise:
    advertising, to the physician at least one of:
        the card, or
        the healthcare information technology product.

12. The system of claim 8, wherein the healthcare organization comprises a preferred-provider organization (PPO) or a health maintenance organization (HMO).

13. The system of claim 8, wherein the healthcare information technology product comprises an electronic medical record.

14. An article of manufacture including a computer-readable medium having instructions stored thereon, execution of which by a computing device causes the computing device to perform operations comprising:

receiving, at a transactional card provider, an endorsement of a healthcare information technology product by a healthcare organization;

identifying a supplier of the healthcare information technology product that accepts a card issued by the transactional card provider;

negotiating, with the supplier, a discount that applies when the healthcare information technology product is purchased with the card; and sending a message to the healthcare organization, wherein the message contains information regarding the discount.

15. The article of manufacture of claim 14, wherein the message further comprises information regarding an additional discount that applies to a physician that purchases the healthcare information technology product using the card.

16. The article of manufacture of claim 15, wherein the healthcare information technology product is designed to bring the physician into compliance with a governmental regulation.

17. The article of manufacture of claim 14, wherein the operations further comprise:

advertising, to the physician, at least one of:
    the card, or
    the healthcare information technology product.

18. The article of manufacture of claim 14, wherein the healthcare organization comprises a preferred-provider organization (PPO) or a health maintenance organization (HMO).

19. The article of manufacture of claim 14, wherein the healthcare information technology product comprises an electronic medical record.

20. A system comprising:

means for receiving, at a transactional card provider, information regarding an endorsement of a healthcare information technology product by a healthcare organization;

means for identifying a supplier of the healthcare information technology product that accepts a card issued by the transactional card provider;

means for negotiating, with the supplier, a discount that applies when the healthcare information technology product is purchased with the card;

means for sending a message to the healthcare organization, wherein the message contains information regarding the discount.

21. The system of claim 20, wherein the message further comprises information regarding an additional discount that applies to a physician that purchases the healthcare information technology product using the card.

22. The system of claim 20, wherein the healthcare information technology product is designed to bring the physician into compliance with a governmental regulation.

23. The system of claim 20, further comprising:

means for advertising, to the physician, at least one of:
    the card, or
    the healthcare information technology product.

24. The system of claim 20, wherein the healthcare organization comprises a preferred-provider organization (PPO) or a health maintenance organization (HMO).

25. The system of claim 20, wherein the healthcare information technology product comprises an electronic medical record.

* * * * *

UNITED STATES PATENT AND TRADEMARK OFFICE
CERTIFICATE OF CORRECTION

PATENT NO. : 7,949,543 B2  
APPLICATION NO. : 11/674437  
DATED : May 24, 2011  
INVENTOR(S) : Chan et al.

Page 1 of 1

It is certified that error appears in the above-identified patent and that said Letters Patent is hereby corrected as shown below:

Column 8, line 38, in Claim 7, delete "cardmember." and insert -- card member. --.

Signed and Sealed this
Fourth Day of October, 2011

David J. Kappos
*Director of the United States Patent and Trademark Office*